(12) United States Patent
Gutridge et al.

(10) Patent No.: US 6,830,335 B2
(45) Date of Patent: Dec. 14, 2004

(54) OPHTHALMOSCOPE LASER ATTACHMENT

(75) Inventors: John Robert Gutridge, Hampton (GB); Timothy Ralph Snellgrove, Stockport (GB)

(73) Assignee: Litechnica Limited, Middlesex (GB)

( * ) Notice: Subject to any disclaimer, the term of this patent is extended or adjusted under 35 U.S.C. 154(b) by 82 days.

(21) Appl. No.: 10/207,372

(22) Filed: Jul. 29, 2002

(65) Prior Publication Data

US 2004/0017545 A1 Jan. 29, 2004

(51) Int. Cl.⁷ .............................. A61B 3/10; A61B 3/00
(52) U.S. Cl. .......................... 351/221; 606/4; 606/17; 600/558; 351/246
(58) Field of Search .......................... 351/200, 205, 351/206, 214, 221, 246; 600/558; 606/4–6, 10, 13, 17, 18; 128/898

(56) References Cited

U.S. PATENT DOCUMENTS

| | | |
|---|---|---|
| 4,397,310 A | 8/1983 | Pomerantzeff |
| 4,580,559 A | 4/1986 | L'Esperance |
| 5,252,999 A | 10/1993 | Sukigara et al. |
| 5,479,222 A | 12/1995 | Volk |
| 5,784,147 A | 7/1998 | Volk |
| 5,805,269 A | 9/1998 | Volk |
| 5,817,088 A * | 10/1998 | Sterling ...................... 351/205 |
| 5,940,166 A * | 8/1999 | Miller ...................... 351/221 |
| 6,168,274 B1 | 1/2001 | Matthews |
| 6,186,628 B1 | 2/2001 | Van De Velde |
| 6,280,033 B1 | 8/2001 | Pedack |
| 2002/0029033 A1 | 3/2002 | Eberhard et al. |

* cited by examiner

Primary Examiner—Linda C. M. Dvorak
Assistant Examiner—John R Sanders
(74) Attorney, Agent, or Firm—Mintz, Levin, Cohn, Ferris, Glovsky and Popeo, P.C.

(57) ABSTRACT

A binocular indirect laser ophthalmoscope is provided comprising binocular eyepieces each having an optical axis defining an optical plane, the ophthalmoscope having a central viewing axis lying in the optical plane; and an optical element adapted to position a laser beam into the optical plan substantially on the viewing axis and substantially parallel to the viewing axis.

30 Claims, 13 Drawing Sheets

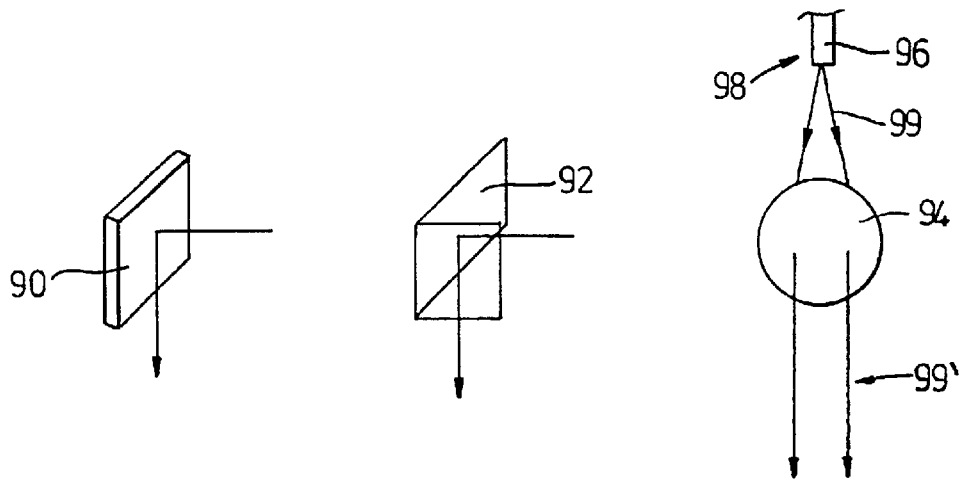
Fig. 9A   Fig. 9B   Fig. 9C
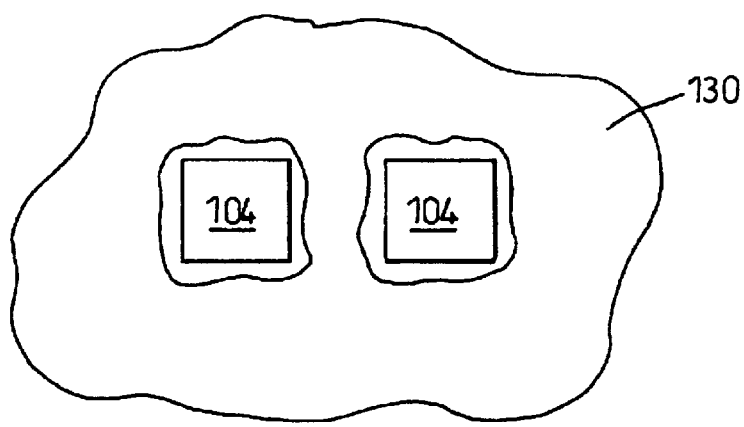
Fig. 10D
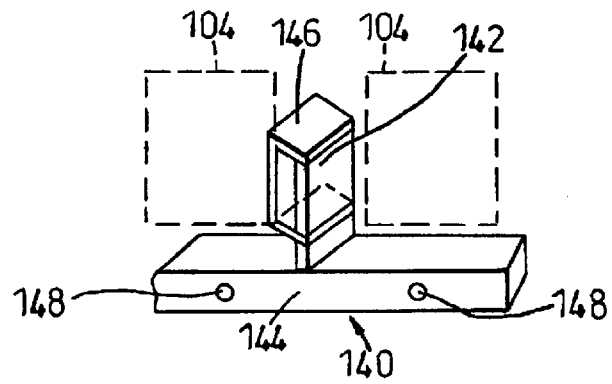
Fig. 11

OPHTHALMOSCOPE LASER ATTACHMENT

BACKGROUND OF THE INVENTION

The present invention relates to a binocular indirect ophthalmoscope and to a laser accessory therefor.

Ophthalmologists need to examine the retina for a number of reasons. An indirect ophthalmoscope is one of a number of devices used for this purpose. An indirect ophthalmoscope is, typically in essence, a pair of viewing binoculars, for example with 2× magnification, mounted on a headband with an integrated light source for projecting light into the patient's eye to enable the retina to be viewed by a clinician wearing the ophthalmoscope.

It is known to integrate a laser into the headset of the ophthalmoscope in order to treat disorders observed by the clinician, for example by a photocoagulation treatment of a peripheral portion of a patient's *fundus oculi*.

The design of an attachment for providing a laser beam, conventionally involves an optical fibre delivery system for connection to the laser and an associated set of optical elements for focussing the divergent beam from the fibre's distal end to the patient's eye. These may include, dependent on design, a lens for converging the laser beam and possibly a mirror for deflecting the beam out to the patient at a distance of approximately 30 centimetres in front of the ophthalmoscope.

Whatever the delivery method, the output elements of the laser delivery system need to be secured in front of the ophthalmoscope.

Hitherto no one has been able to mount the laser delivery coaxial with the viewing path due to the mechanics of the laser delivery. Having the laser coaxial with the vision is the ideal scenario for the surgeon.

The final deflecting mirror or lens has always been mounted above or below the line if sight in order to preclude obstruction of the surgeons view. The beam therefore converges into the eye at an angle rather than being in the visual plane of the ophthalmoscope.

The mounting of the output optics in front of the ophthalmoscope has been a major problem as the goal is to achieve coaxiality with the vision.

Introducing the laser from above the line of sight of the ophthalmoscope at 12 o'clock necessitates having a mirror angled at 45 degrees to the vertical plane. This is secured on a shaft in the opposite plane if movement of this mirror is to be achieved. A rotatable shaft with a cam mechanism is often employed to tilt the mirror to the required position. This shaft would obscure the vision of the ophthalmoscope if it were in the plane of his line of sight. This alone necessitates the mirror assembly to be mounted above or below the line of vision.

It is possible that if the line of vision is directed through the centre of a patient's pupil, the laser-beam, which is angled to the line of vision, may clip the patient's iris.

This is a common problem and clinicians use eye drops in order to dilate the pupil as much as possible in order to reduce this disadvantage. Unfortunately diabetics have glycogen disorders within the iris structure and dilation is not always possible which hinders further the procedure. If the laser beam were coaxial with the viewing optics the problem would be greatly alleviated.

Accordingly known laser beams projected from the ophthalmoscope are not parallel with the optical axes of the binocular. They converge at an angle of about 5 to 10 degrees.

SUMMARY OF THE INVENTION

It is a principal object of this invention to provide an alternative laser delivery means for an indirect ophthalmoscope.

According to a first aspect the invention comprises a binocular indirect laser ophthalmoscope comprising binocular eyepieces each having an optical axis defining an optical plane, the ophthalmoscope having a central viewing axis lying in said optical plane; and an optical element adapted to position a laser beam into said optical plane substantially on said viewing axis and substantially parallel to said viewing axis.

According to a second aspect the invention comprises a laser-directing attachment for attaching to an indirect ophthalmoscope comprising: an attachment mechanism adapted to attach said attachment to the ophthalmoscope; a laser fibre connector adapted to connect to an optical fibre adapted to carry a laser beam; a director adapted to direct a laser beam in a direction relative to said attachment; and direction controls adapted to control the director to place a laser beam emitted via said connector in a line generally superimposed upon a central viewing axis of said indirect ophthalmoscope.

According to another aspect of the invention a binocular laser indirect ophthalmoscope comprises: a pair of eyepieces for a user to look through, and respective image capture optics associated with respective eyepieces, said eyepieces and associated image capture optics having respective optical axes, said optical axes defining an optical plane, and there being a central line of view of said ophthalmoscope lying in said optical plane; a laser beam coupler for coupling a laser beam delivery device to said ophthalmoscope; a laser beam director for directing a laser beam provided from said laser beam coupler forwards, away from said ophthalmoscope; an adjustment mechanism for controlling the position or orientation of said laser beam director so as to vary the position or direction of a laser beam propagating from said director; and wherein said laser beam coupler is provided disposed laterally to one side of said image capture optics and said laser beam director is provided in front of said image capture optics, and wherein said adjustment mechanism is adjustable to position a laser beam propagating from said director substantially in said optical plane of view, substantially undivergent therefrom and substantially on said central line of view.

According to another aspect the invention comprises a device for attachment to an indirect ophthalmoscope for fitting a laser to said ophthalmoscope, said device comprising: a support member; an attachment formation provided associated with said support member for attaching said support member to said ophthalmoscope; a laser director coupled to said support member by a mechanical coupling mechanism so as to be movable relative to said support member;, a control mechanism for moving said laser director relative to said support member; wherein said device has a forward-facing front portion away from which a laser beam is directed in use, and a rearward facing pack portion which in use is disposed towards an operator's face, and a side portion laterally disposed to one side of said device; and wherein said mechanical coupling mechanism is provided at said side portion.

According to another aspect the invention comprises a method of aligning a laser beam of an indirect binocular laser ophthalmoscope with a visual plane of said ophthalmoscope defined by first and second optical axes of first and second eyepiece optics of said binocular ophthalmoscope, said method comprising providing a reflector between said optical axes such that said reflector intersects said visual plane; directing a laser beam onto said reflector at about the position where said reflector intersects said visual plane; and controlling the orientation or position of said reflector so as to cause a laser beam reflected from said reflector to be in or parallel to said visual plane.

Preferably the binocular ophthalmoscope has a central viewing axis and the method comprises emitting the laser beam generally on the viewing axis.

According to another aspect the invention comprises a method of aligning a laser beam of an indirect binocular laser ophthalmoscope with a visual plane of said ophthalmoscope defined by first and second optical axes of first and second eyepiece optics of said binocular ophthalmoscope, said method comprising providing a beam manipulator between said optical axis, such that said beam manipulator intersects said visual plane, and causing said laser beam to enter said ophthalmoscope laterally to one side thereof.

According to another aspect the invention comprises a method of laser treatment of an eye by controlling the position at which a laser beam encounters a structure of said eye by using an indirect ophthalmoscope having a laser director optical element, by providing said laser beam from the side of said ophthalmoscope and providing said optical element substantially in a vertical plane inclined at about 45° to a line of propagation of said laser beam, thereby directing said laser beam away from said ophthalmoscope substantially in and parallel to a plane defined by optical axes of binocular optics of said ophthalmoscope.

According to another aspect the invention comprises a method of laser treatment of an eye comprising controlling the position at which a laser beam encounters a structure of said eye by using an indirect ophthalmoscope having a laser director optical element provided in a frame, the user looking through said frame at the eye to be treated; bodily moving said frame so as to move the path of said laser beam to lie in or parallel to a visual plane defined by optical axes of the binocular optics of said binocular ophthalmoscope; and activating said laser beam.

According to another aspect the invention comprises a method of controlling the angle of a laser beam relative to a viewing plane of a binocular laser ophthalmoscope, said viewing plane being defined by first and second optical axes of respective first and second optical pathways of said binocular ophthalmoscope, said method comprising providing an optical element on a carrier mounted on said ophthalmoscope; looking through said carrier; moving said carrier relative to other parts of said ophthalmoscope so as to move said optical element thereby altering the angle at which said laser beam will propagate relative to said visual plane.

According to another aspect of the invention a binocular indirect ophthalmoscope has first and second image capture optics having respective first and second optical pathways which define a viewing plane, and delivery means for delivering a laser beam to an optical element located adjacent said image capture optics for causing said laser beam to be emitted in a direction substantially in said viewing plane, undivergent therefrom.

According to another aspect the invention comprises a binocular indirect ophthalmoscope having a central viewing axis lying in a viewing plane which contains the optical axes of the binocular optics, and means for delivering a laser beam in that plane to an optical element for deflecting said laser beam to a direction substantially on and parallel to said viewing axis.

According to another aspect the invention comprises a binocular indirect ophthalmoscope whose eyepieces have optical axes which define a viewing plane, a mirror carrier frame which has a viewing opening or window registered with said eyepieces and has a dichroic mirror mounted in that viewing plane extending across said viewing opening, and delivery means for delivering a laser beam to said mirror for reflection into said viewing plane and along a central viewing axis of said ophthalmoscope.

According to another aspect the invention comprises an accessory for a binocular indirect ophthalmoscope which comprises a frame having viewing openings located to either side of a reflective surface, and directing means for directing a laser beam onto said reflective surface for reflection into a viewing direction.

According to another aspect the invention comprises an accessory for a binocular indirect ophthalmoscope which comprises a frame having a viewing aperture and an optical element disposed across said viewing aperture, said optical element being adapted to reflect light of a selected laser wavelength and transmit light of at least another selected optical wavelength such that in use a user is able to look through said viewing aperture and through said optical element.

Said reflecting surface, or other optical element, may be mounted as a central bridge piece of a cage or carrier which defines viewing openings in register with each said eyepiece and to each side of the reflective surface (or optical element). Alternatively, said reflecting surface, or other optical element may be disposed in front of said viewing aperture/openings and the user may look through said optical element.

The cage or carrier is preferably adjustable in angle about an axis which lies in, or is parallel with, the said viewing plane and which is substantially normal to said central viewing axis.

In an embodiment of the invention the laser beam is delivered substantially normal to said line of sight and is reflected onto the line of sight by a mirror mounted to said cage. This allows an optical fibre infeed to be brought down from overhead. This is an arrangement which is more convenient for the user.

The means for delivering the laser beam is preferably arranged also to deliver an aiming beam of a visible light, e.g. from a diode. Such a visible light beam may be used as an aiming marker for any laser treatment to be carried out.

Any suitable laser may be used.

The apparatus preferably includes dichroic filters which are interposed between the laser light path and eyepieces of the binocular. This will protect the eyes of the clinician from any laser light reflected back from the eye of the patient.

BRIEF DESCRIPTION OF THE DRAWINGS

The invention will now be described in greater detail with reference to the accompanying drawings in which:

FIG. 5' shows a modification of the arrangement of FIG. 5;

FIGS. 9A to 9C show different optical elements for controlling laser beams;

FIG. 10D shows schematically areas that are out of the image—capture area of an ophthalmoscope;

FIG. 11 shows an attachment for an ophthalmoscope where the optical element is not adjustable.

DESCRIPTION OF PRIOR ART

Figure 1:
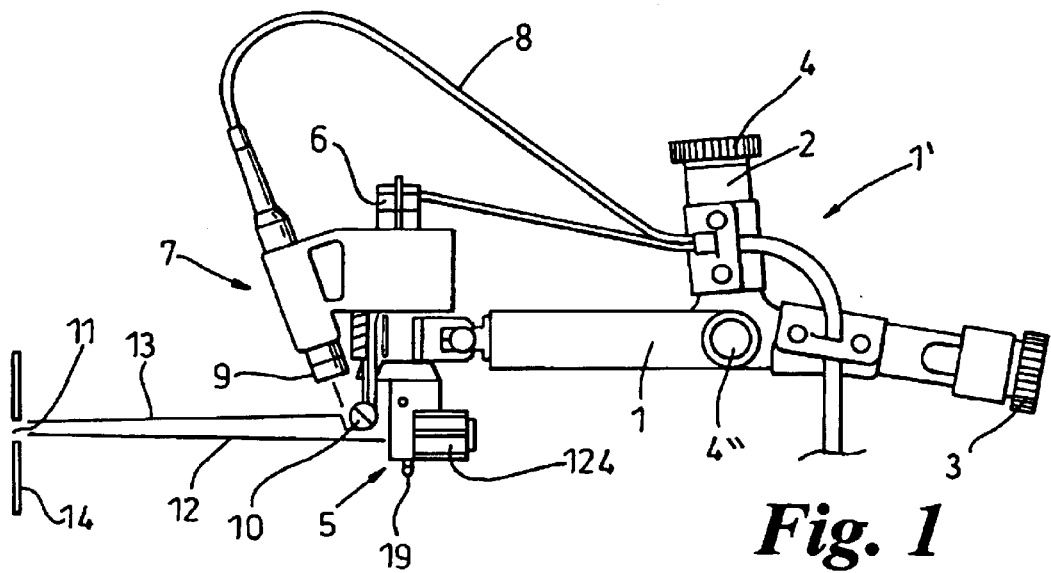
FIG. 1 illustrates a typical known indirect ophthalmoscope with a laser attachment as known in the art.
Figure 2:
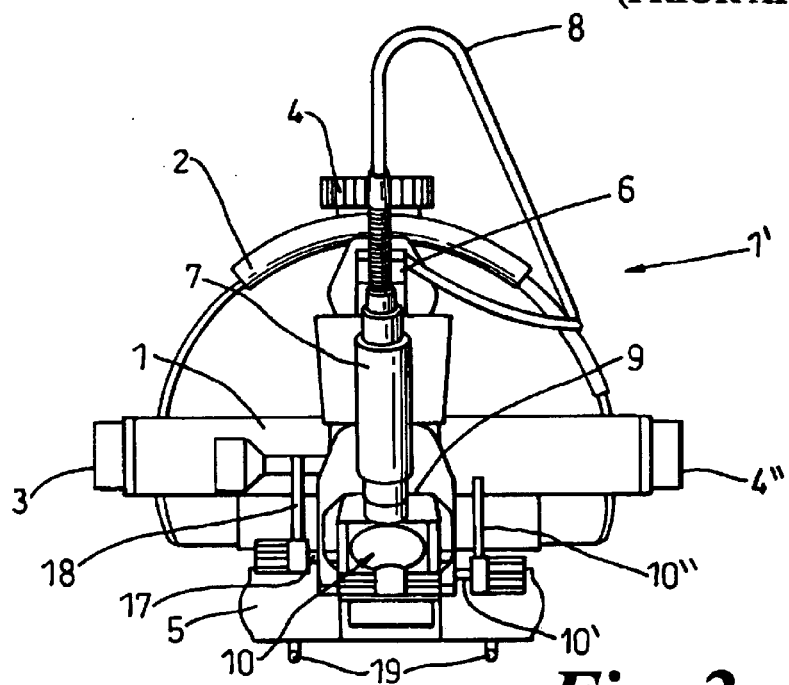
FIG. 2 illustrates the indirect ophthalmoscope of FIG. 1 from the front.

In FIGS. 1 and 2 an indirect ophthalmoscope head set 1' comprises a horizontal headband 1, a vertical headband 2, knobs 3 and 4 for adjusting those headbands, an overband 4' and an overband knob 4". At the front of the horizontal headband 1 is mounted a binocular generally indicated at 5. The binocular has first and second optical pathways 5a and 5b, with associated optical axes, shown as 5c and 5d in FIG. 3C. The optical axes 5c and 5d of the binoculars define a plane, 5e, termed the plane of view. A source of illumination 6, such as an electric lamp, is provided above the binocular for illuminating the eye of the patient.

A laser attachment is generally indicated at 7. This comprises an optical fibre 8 of typically 100 μm diameter, a focusing, or objective, lens 9 and a mirror 10 for reflecting the laser through the pupil 11 of the patient's eye.

The mirror 10 is mounted on a rod 10'. A lever 10" is coupled to the rod 10' and is manually adjusted by the user to tilt the laser beam up and down. Because the mechanism required for supporting and tilting the mirror 10 has a width such that it would necessarily obstruct the clinician's view if it were located in the plane of vision 12, it is located above that plane of vision so that the reflected laser path 13 converges with the plane of vision for example at the retina. Consequently, the path of the laser 13 is spaced from the plane of vision 12 where it enters the pupil and there is accordingly a risk that the laser may clip and injure the iris 14 of the patient.

As shown in FIG. 2, the indirect ophthalmoscope also has an illumination mirror 16 mounted on a rod 17, an illumination mirror adjustment lever 18 adapted to move the rod 17 angularly, and interpupillary adjustments 19. White light illumination is provided into the patient's eye using the illumination mirror.

It will be appreciated that the lower mirror 10 is angularly movable about a horizontal axis coming out of the page, as seen in FIG. 1 (parallel to the plane of the page in FIG. 2). The user manually moves lever 10" to move the mirror 10 angularly to move the laser beam up and down, as seen in FIG. 1. The mirror 10 is inclined at about 45° to the line of sight of the binoculars 5.

Figure 3A:
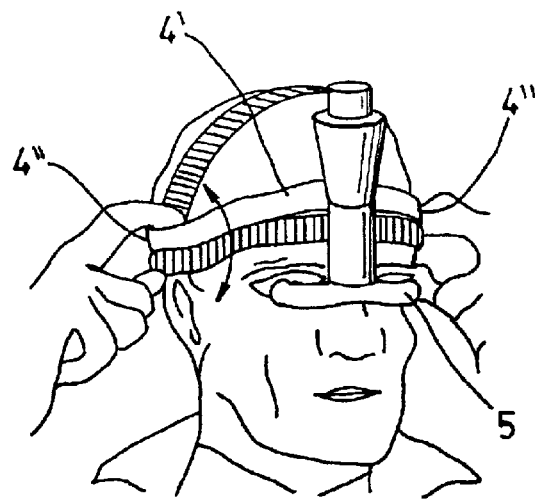
FIG. 3A illustrates schematically how an indirect ophthalmoscope is worn by a user.
Figure 3B:
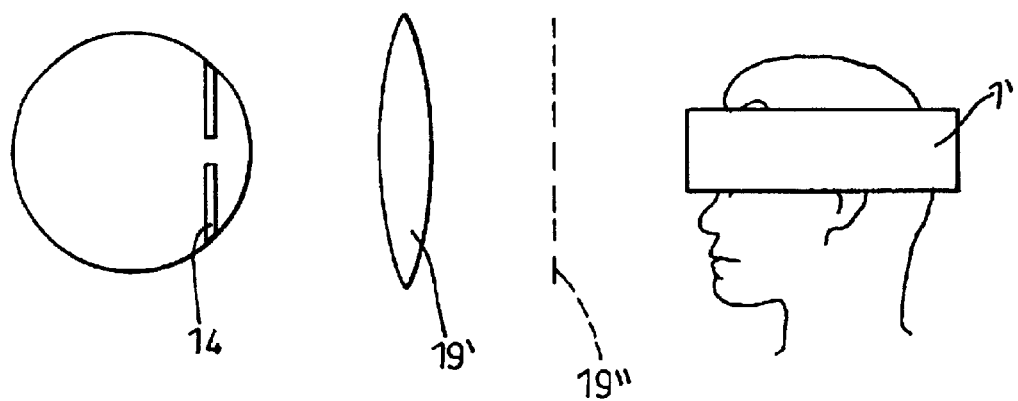
FIG. 3B illustrates the use of the ophthalmoscope of FIG. 1.
Figure 3C:
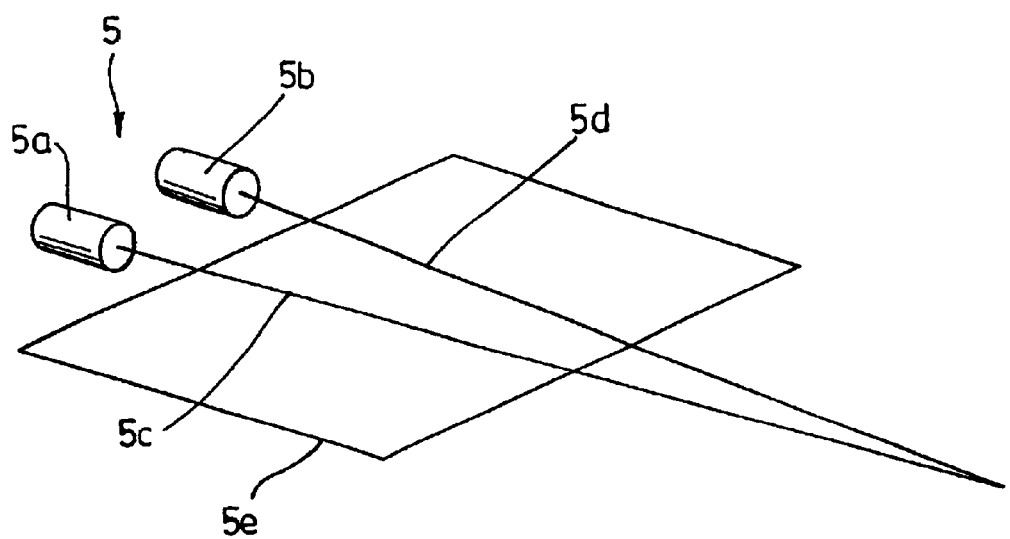
FIG. 3C illustrates binocular axes of an ophthalmoscope and a plane of view.

In practice the ophthalmoscope 1' is used, as shown in FIG. 3B, in conjunction with a lens 19', for example of about 20 diopter which produces a floating image 19" of the patient's eye 30 cm or so in front of the indirect ophthalmoscope.

DESCRIPTION OF A PREFERRED EMBODIMENT OF THE INVENTION

Figure 4:
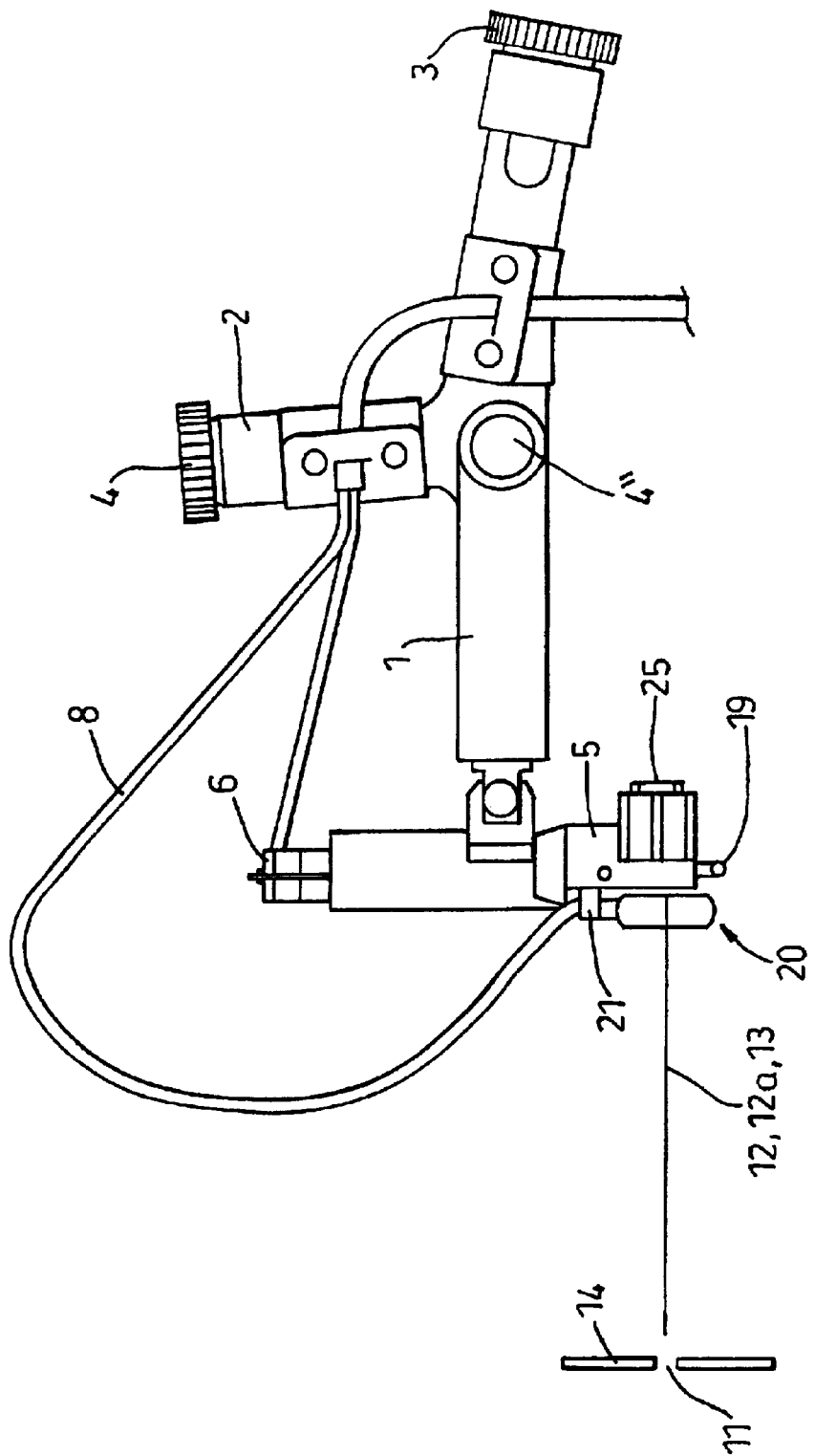
FIG. 4 illustrates an indirect ophthalmoscope according to the present invention.
Figure 5:
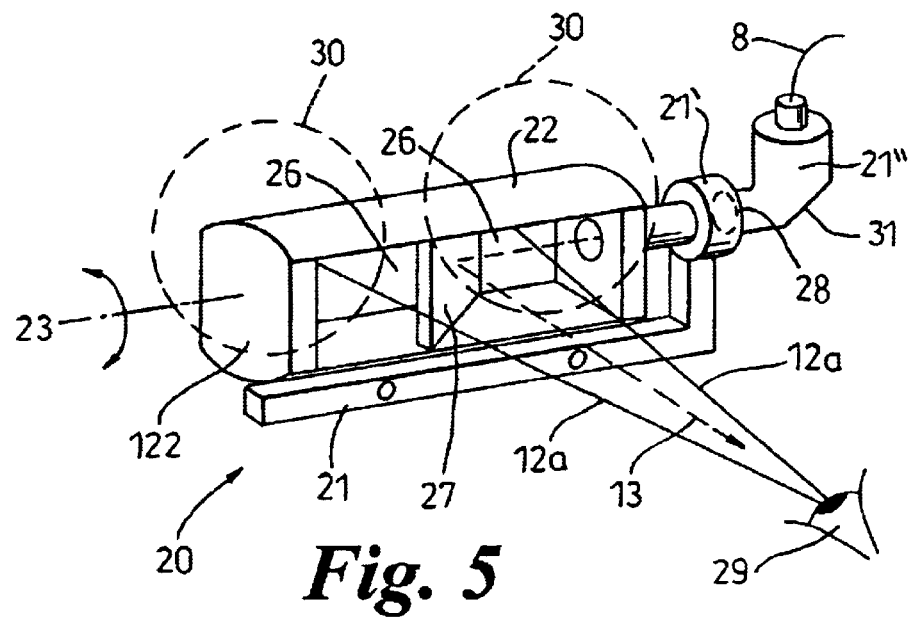
FIG. 5 is a detailed view of a laser attachment in accordance with the invention for fitting to an ophthalmoscope to provide an indirect laser ophthalmoscope.
Figure 5:
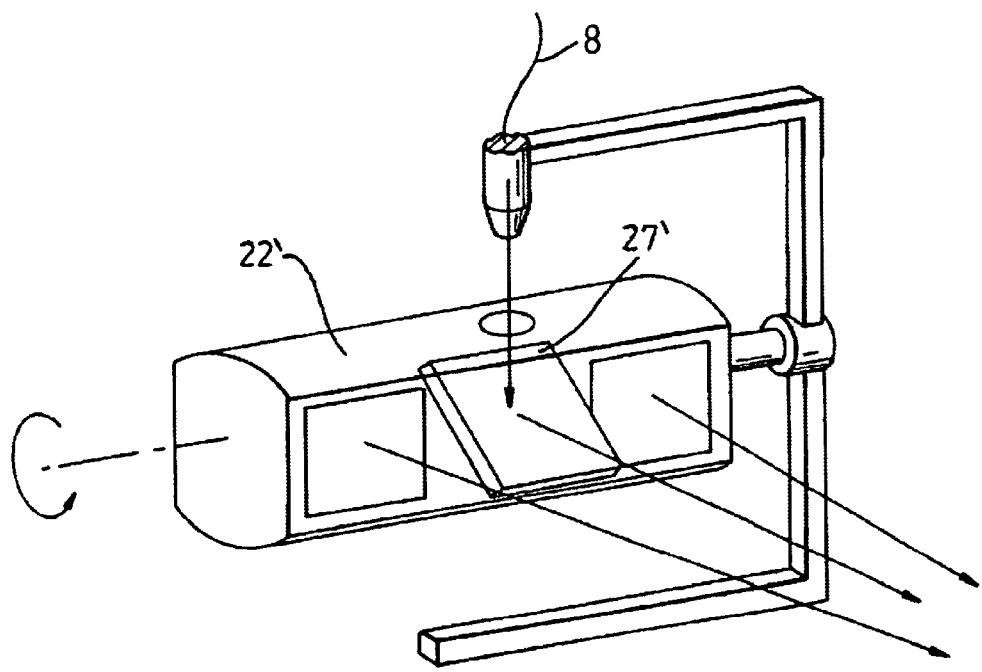

The present invention avoids the problem of clipping the iris by ensuring that the reflected path 13 of the laser coincides with, or is parallel to, the plane 12 defined by the optical axes 12a of the binocular eyepieces as shown in FIGS. 4 and 5.

In FIG. 4 parts of a conventional indirect ophthalmoscope are allotted the same reference numerals as given in FIG. 1. A laser attachment 20 is provided secured, (preferably releasably secured, e.g. by screws) to the binocular 5 by a bracket 21. This laser attachment is shown in greater detail in FIGS. 6 and 7.

Figure 10A:
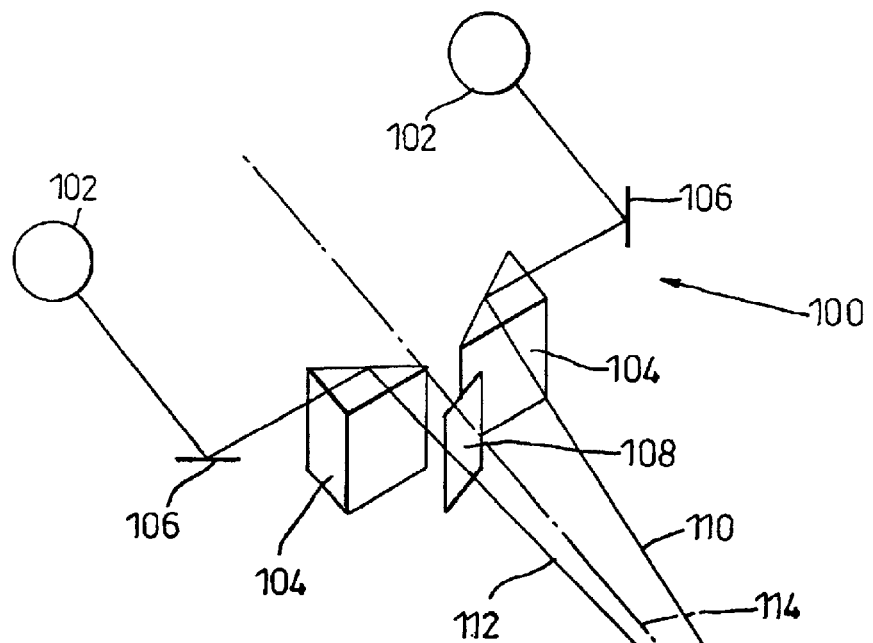
FIGS. 10A to 10C shows a schematic perspective view, front view and plan view of an ophthalmoscope fitted with an attachment in accordance with the invention.

In FIG. 5 it will be seen that the laser attachment 20 comprises a carrier, or frame, or cage 22 mounted to the bracket 21 in that such a way that it is pivotable about an axis 23 lying in the same plane as the optical axes 12a of the eyepieces 25 (see FIG. 2) of the binocular 5 (or more precisely, in the same plane as the optical axes of image-capturing optics (e.g. prisms) of the binoculars—see FIG. 10A). That is to say, in FIG. 5 the carrier frame 22 is angularly movable about a horizontal axis. The carrier 22 defines viewing openings 26 to each side of an optical element 27 in this example a mirror 27, which is carried by the carrier frame 22 and is located in the plane defined by the optical axes 12a, and transverse thereto. That is to say, in FIG. 5 the mirror is in a generally vertical plane and is inclined at about 45° to a horizontal line. Laser light is delivered in the viewing plane through optical fibre 8 via focusing lens 28 onto the mirror 27, where it is reflected, still in the viewing plane, along axis 13 to the eye 29 of the patient. Journal 21' pivotally mounts the frame 22 to the bracket 21. The journal 21 has an adapter 21" which releasably couples an optical fibre 8 to the attachment 20. As the frame 22 moves angularly the fibre 8 remains stationary and aligned with the pivot axis 23 of the frame.

It will be appreciated that the central point of the laser directing mirror 27 is provided in a line directly between the eyepieces (or image—capturing optics) of the binoculars. Instead of having the mirror 27 mounted on a bar, and having to provide a way of moving the bar angularly, the mirror is mounted in the frame 22, and the whole frame 21 is moved angularly. This allows us to put the frame-pivoting and frame manipulating, mechanism outside of the line of sight of the user—laterally outside of the path of light that is gathered by the image—capturing optics of the binoculars. The user looks through the frame, and his line of sight is not impaired as the frame is moved.

The laser beam reflected from the mirror 27 can truly be co-incident with the central line of sight of the user, instead of being inclined relative to it.

If it is found more convenient for the optical fibre 8 delivering the laser beam to come in from the overhead direction a mirror indicated at 31 may be provided for reflecting the incoming laser beam into the viewing plane.

FIG. 5' shows a modification in which the mirror 27' is inclined in a direction akin to the prior art, but in which the user still looks through the frame 22', and in which the frame is rotated, carrying the mirror with it, rather than just the mirror. Again, the mirror can reflect a beam of laser light parallel to the plane/line of sight.

The arrangement of FIG. 5 is considered better than that of FIG. 5'. One reason is because the laser fibre 8 of FIG. 5 is on the axis of rotation of the frame 22, and this simplifies the mechanics of coupling the fibre 8 to the frame 22.

It will be noted that the mirror 27 of FIG. 5 is mounted in a vertical plane, that is, a plane normal to the viewing plane, and that this mirror plane is aligned at 45 to the axes 12a of the binocular eyepieces. This allows the central point of the mirror to be located between the viewing eyepieces with no visual obstructions for the clinician. The mirror 27 may be rotated for adjustment of the alignment of the axis 13 of the laser beam by pivoting the cage 22 about the axis 23.

Dichroic filter elements, schematically shown as reference 30, may be fitted to the rear of the cage, or to the eyepieces of the binocular. A preferred laser is a KTP laser having a wavelength of 532 nanometres. The binocular suitably has a 2× magnification and incorporates the interpupilliary mechanism 19 for adjusting the spacing of the eyepieces 25 to accommodate variations in eye spacing of different users.

The laser attachment 20 may readily be attached to any conventional indirect ophthalmoscope by its bracket 21, using an intermediate adaptor (not shown) if necessary. Laser beam input can be via a conventional optical fibre feed and the attachment 20 may therefore be used for coupling any suitable laser device into such an ophthalmoscope. All that is needed is a suitable connector 21" and an optical fibre 8 (with appropriate connection to connect to the laser).

The optical fibre 8 suitably also carries a beam of a visible light, for example from a diode light source, which also travels along axis 13 so that the clinician has an aiming marker which will not affect the eye of the patient, but will give an indication of the target point of the laser beam when that is selectively triggered. The laser beam is, of course, not normally operating through the indirect ophthalmoscope, only being effectively emitted to the ophthalmoscope, and cutting/burning/sealing, when the clinician activates it. The laser will usually be "on" and some stop/shutter mechanism will be opened by the clinician to operate on the eye (typically a foot switch).

Figure 6:
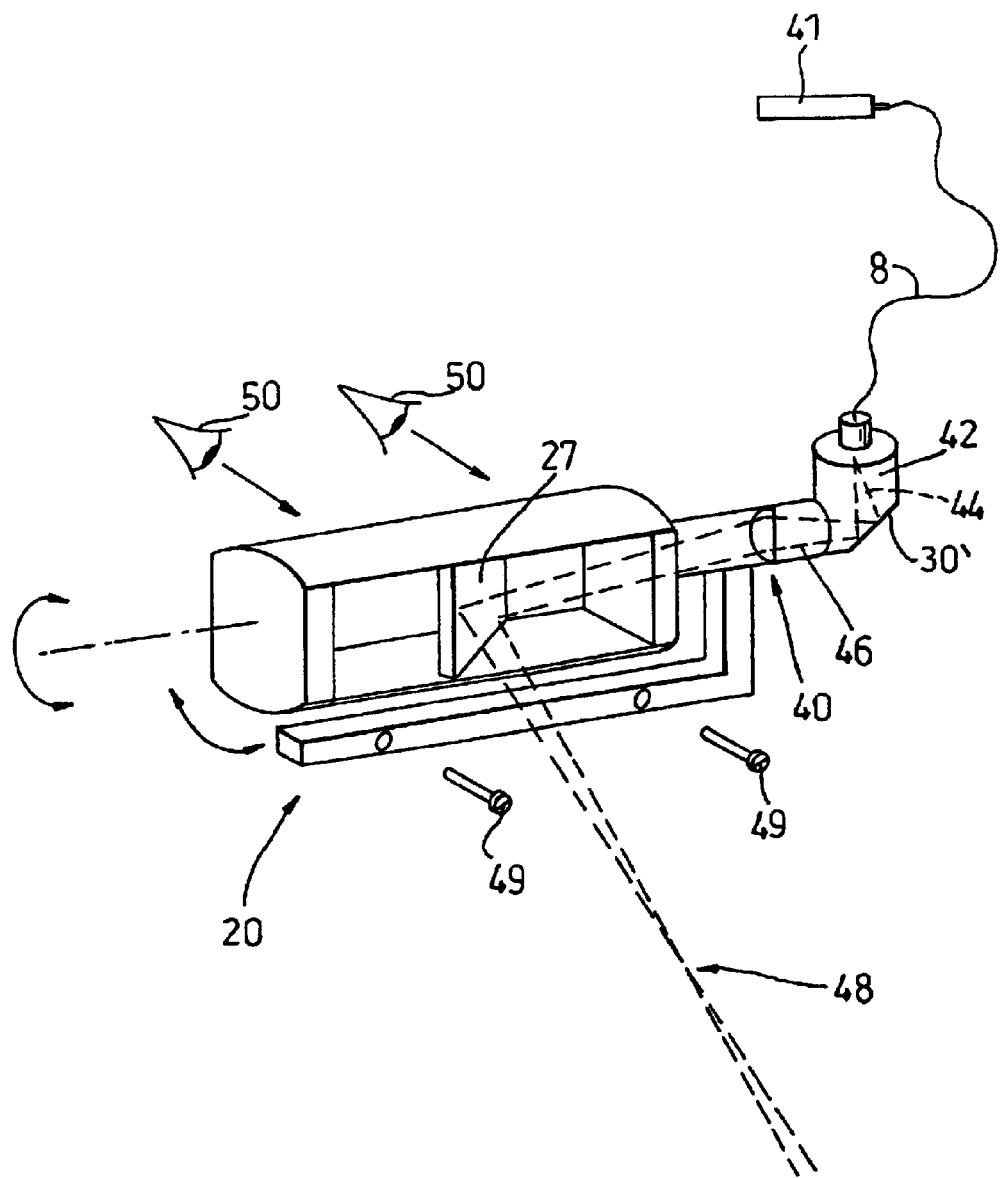
FIG. 6 shows a variant of the arrangement of FIG. 5.

FIG. 6 shows a finer detail of the arrangement of the attachment 20 of FIG. 5. This shows that there is a lens 40 of variable focus, with the focus controlled by the user (e.g. by a hand-operated wheel or knob). A laser 41 is coupled to the attachment via fibre 8. A coupling, referenced 42, produces a diverging beam 44 of laser light which is reflected off mirror 30', still diverging at 46. The lens 40 focuses the beam of laser light, which is reflected off the mirror 27 to a focal point 48. The focal point is intended to be on the retina, or other structure of the patient's eye, to be burned/treated. Fixing screws 49 are shown for attaching the attachment 20 to an indirect ophthalmoscope. The clinician's eyes are referenced 50.

Figure 7:
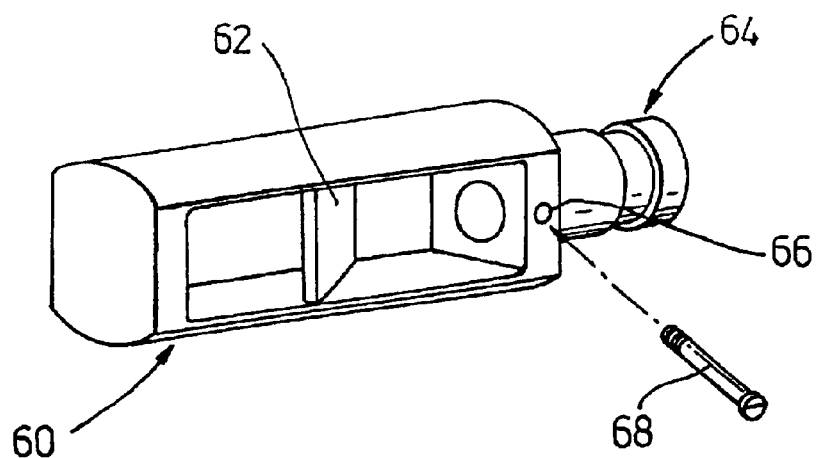
FIG. 7 shows more detail of a housing for a mirror of the indirect ophthalmoscope of FIG. 4.

FIG. 7 shows a mirror carrier 60, carrying a mirror 62 angled at 45° sideways, journalled for angular movement by journal 64, and a hole 66 possibly screw threaded, for receiving a turning lever 68 to enable a user to rotate the carrier 60. The lever 68 is normally attached to the carrier 60.

Our attachment, and a laser indirect ophthalmoscopes fitted with it, enables the laser beam to be emitted on the central viewing axis of the binoculars, in the same plane as the binocular plane of sight, rather than being inclined to it. This means that there is less danger of clipping the iris. This in turn means that treatments can be performed faster. Typically a patient is given eye drops to cause their pupil to widen, and a wait is necessary for them to act (perhaps 20 minutes). It is no longer necessary to have the pupil quite so wide in some circumstances using the present invention; and so patients who's pupils are not so dilated can be treated. This can speed up throughput of patients in a clinic/surgery.

Previously, clinicians used the laser mirror control to alter the convergence angle, and convergence distance, of the laser (relative to the plane of the optical axes of the binoculars. Now clinicians alter the laser mirror in order to try to get the laser beam in the plane of the optical axes of the binoculars so that there is no, or substantially no, divergence.

In the embodiments described the laser output mirror is housed within a frame that surrounds, or skirts, the outside of the vision area (the ×2 viewing components of the binoculars). The laser is introduced laterally (as opposed to vertically as with prior art designs which introduce the laser from above) through a lens, onto the angled 45° output mirror, deflecting the converging beam towards the patient.

We may fold the laser back vertically using a side mirror to allow the fibre to be introduced at 12 o'clock. Bringing the fibre in sideways may be inconvenient to the user.

The mounting of the laser-reflecting mirror at about 45°, sideways is an important aspect of one embodiment. In this configuration, with no horizontal tilt mechanism, it allows us to mount the mirror with no visual obstruction and thus making it truly coaxial; this will be a major benefit to the ophthalmologist.

We are able to move the mirror vertically, by rotating the frame, which holds the mirror, around a joint actuated by a small lever. The mirror is invisible to the user, being between the viewing optics. With no horizontal tilt mechanism, there is no associated viewing obstruction.

Moreover our attachment fits ×2 popular indirects. (e.g. the All pupil and Vantage made by Keeler Optical). Unlike other laser attachments which have to be factory integrated our attachment is held on easily by mounting screws. The attachment can be fitted to an existing indirect ophthalmoscope by the user themselves, presenting a big financial saving over integrated laser indirects.

Additionally our attachment will interface with any laser. Prior art indirect laser headsets are designed by the laser manufacturer and are dedicated to their laser and are not interchangeable with other lasers. Our design allows the user to purchase a product that is not exclusive to any specific laser.

The laser beam delivered to the mirror is preferably provided in, or substantially in, the plane of view.

In summary, in one embodiment a binocular indirect ophthalmoscope has eyepieces which have optical axes defining a viewing plane. Means is provided for delivering a laser beam in that plane and on the central visual axis of the binoculars. This may be achieved by delivering a laser beam to a reflective surface located between the eyepieces, or in front of the eyepieces, provided for directing the laser beam to be coincident with the viewing axis. The cage may be, in some embodiments, adjustable in angle about an axis in the viewing plane and a substantially normal to the central viewing axis. The user looks through or past, a frame that holds the optical element that controls the laser beam, the frame being outside of the user's vision.

A non-exhaustive list of possible variants includes:-

Having the frame 22,22—such that it does not completely surround the apertures 26. The frame could simply be above or below the apertures. Indeed, the "frame" could simply be a support for the mirror 27, said support being disposed outside of the field of view/plane of view of the binoculars. It will be appreciated that holding the mirror 27 and its upper and/or lower surface, well out of the way of the plane of the field of view, is advantageous.

Instead of being angularly moveable the frame/carrier 22 could be bodily linearly moveable (e.g. slidable) or a mixture of sliding and angular movement could be used. What is important is that it is possible to control the "vertical" position of the laser beam without having the control mechanism be in the plane defined by the optical axes of the binoculars, and in the field of view of the clinician.

There could be two user-operated (e.g. manually moved) control surfaces (e.g. levers/wheels/projections), one to either side of the frame/carrier/mirror support.

It will be appreciated that the mirror is one example of an optical element that can be used to control/direct a laser beam. Other optical elements could be used instead of/in addition to a mirror including a prism, and/or a lens.

In a simple variant the mirror shown in the previous drawings is replaced by a prism. In other variants the mirror is replaced by an optical fibre delivering a laser beam (or a mounting for an optical fibre to be connected to the carrying frame). An optical fibre delivers a divergent beam of light. It would then be desirable to have an optical element, for example a lens, focusing the beam of light. Thus instead of reflecting the beam of light the optical element could simply focus/defocus it.

It would also be appreciated that although in the previous examples the angle of the mirror relative to the laser beam (or optical element relative to the laser beam) is variable, and can be user-controlled (typically manually controlled), attachments, and ophthalmoscopes, are envisaged in which the mirror/optical element is not movable relative to the attachment/ophthalmoscope—it is reflected at a fixed position. So long as this fixed position is generally on, or very nearly on, the central viewing axis of the binocular ophthalmoscope this will be a good instrument. Having the mirror/optical element movable and being able to control the position of the laser beam enables the user to place the laser beam on the central viewing axis. If it is already on there—because the device has a fixed optical element, and a fixed laser path relative to the optics, and movement of the mirror/optical element may be unnecessary.

Figure 8:
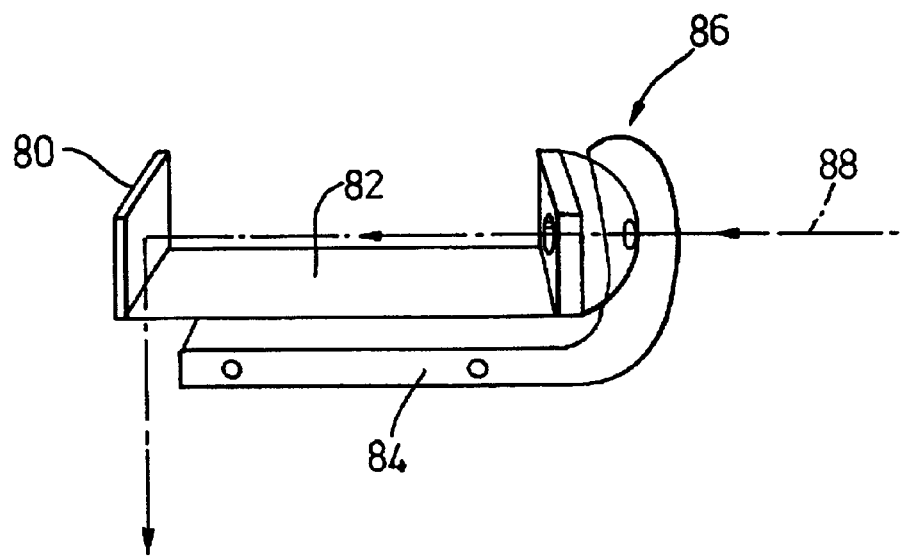
FIG. 8 shows another attachment for an ophthalmoscope.

FIG. 8 shows an alternative attachment (84) for attaching to an ophthalmoscope. This has a mirror 80 (or a prism) mounted on a support (82). The direction of the laser beam 88 is shown coming in through the joint 86, and reflecting off the mirror 80. In this example there is no frame actually surrounding the mirror, and the support 82 is outside of the line of vision of the user ophthalmoscope, and does not obstruct the image-gathering optics.

FIGS. 9A, 9B, and 9C show different optical elements that can be used to condition or direct a laser beam. FIG. 9A shows a mirror 90. FIG. 9B shows a prism 92. FIG. 9C shows a converging lens 94, and a light-limiting end 96 of an optical fibre 98. In the element of FIG. 9C the optical fibre 98, or its end 96 (or a fitting to receive and locate an optical fibre) is provided in the attachment, along with the focussing lens 94. An optical fibre in its diverging beam of light, reference 99, and the lens 94 produces a parallel laser beam, reference 99.

FIG. 10A shows schematically binoculars of an ophthalmoscope 100 having eyepieces 102 through which the clinician looks, image-capturing optical elements 104, in this example prisms, reflecting mirrors 106 which fold the optical path of the light that is gathered/captured by the image-capturing optics 104 and directs it to the eyepieces 102. Also shown schematically is laser-beam deflecting/controlling/conditioning optical element 108 (in this example a mirror). This is disposed, again in this example, slightly in front of the image capturing optics 104 (but it could be level with them, or potentially even within their planned projection.

FIG. 10A also shows the optical axes 110 and 112 of the binoculars, and a central viewing line 114, lying in the plane of the optical axes 110 and 112.

Figure 10B:
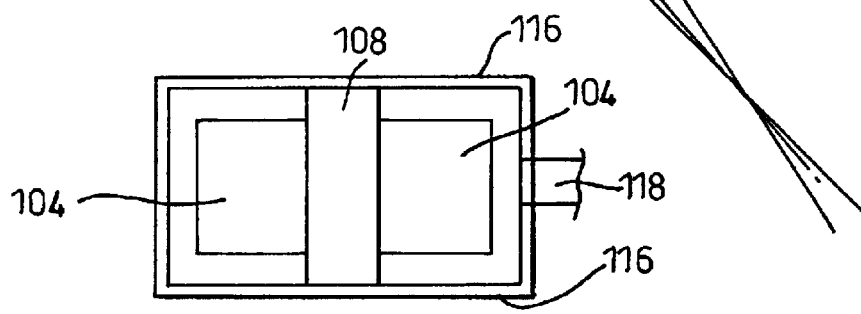

FIG. 10B shows a front view of the arrangement of FIG. 10A. Also shown in FIG. 10B, but not shown in FIG. 10A, is a carrying frame 116 which carries the optical element (e.g. mirror) 108. A spigot 118 is also shown for angularly movably mounting the frame 116.

Figure 10C:
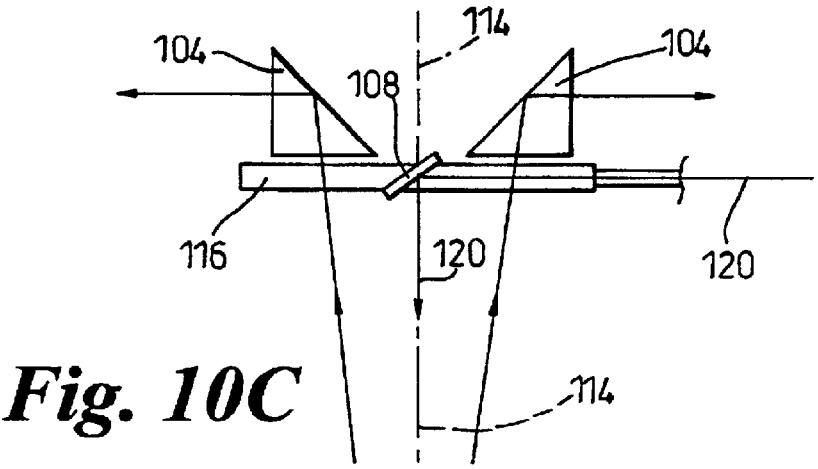

FIG. 10C is a plan view of the arrangement of FIGS. 10A and 10B, also showing a laser beam 120 being reflected off the mirror 108 to be coincident with the central viewing axis 114.

It will be appreciated from FIGS. 10A to 10C that the image captured by the image capture elements (e.g. prisms) 104 is not impaired by the presence of the mirror 108, nor is it impaired by the frame 116 extending around the outside of the prisms: neither the mirror or the frame is in the projected area of the image capture elements 104 when a point in the field of view is traced back to the image capture elements 104.

FIG. 10D is a front view, similar to that of 10B, showing the image capture elements (prisms) 104 and also showing an area 130 surrounding them which is outside of the path of light that is received by the image capture elements 104, and which is therefore available to contain other useful structures of the attachment/and or ophthalmoscope. It will be appreciated there is no real outer boundary to this area.

A laser-absorbing structure is preferably provided behind the mirror (or prism) in case the mirror element breaks. It would be undesirable to have the laser come out of the side of the equipment unchecked. For this reason a laser-absorbing structure (e.g. thick metal wall) is provided either directly behind the mirror, or as part of the frame/carrier. For example wall 122 in FIG. 5 is typically thick enough to absorb the laser beam without allowing the laser beam to burn through.

We prefer to have the eyepieces of the binocular ophthalmoscope removable so as to be able to insert different lenses behind the eyepieces. For example, eyepiece reference 124 in FIG. 1 could unscrew and a different or additional lens could be inserted between the eyepiece and the remainder of the binocular, and the eyepiece then screws back on locating the lens.

Although the laser beam is shown in many of the examples as coming in from the side of the attachments/ophthalmoscope, we envisage arrangements when it could come in from the top, or indeed below.

FIG. 11 shows an attachment 140 for attaching to the front of a binocular ophthalmoscope. A mirror or prism 142 is shown fixedly, non moveably, mounted on mounting beam 144 the mirror is held at its top and bottom edges by a C shaped bracket 146. The support beam 144 is releasably attachable to the front of a binocular ophthalmoscope via threaded screw holes 148.

It will be appreciated that the device of FIG. 11 is not angular moveable about an axis: its orientation relative to the support beam 144 is fixed, and once the support beam 144 has been placed in fixed relationship to the ophthalmoscope to which it is fitted, the angle of the mirror 142 is fixed. So long as when the laser beam falls upon the mirror it is, indeed, reflected generally along the central viewing axis of the binocular ophthalmoscope (and not significantly diverging a above or below the viewing plane, a fixed mirror/optical element arrangement is also envisaged).

Of course, a modification of the arrangement of FIG. 5 could be the fixed mounting of the support frame 22 relative to the carrier 21, there still being a support frame surrounding the mirror, and the clinician still looks through aperture/windows in the support frame. The support frame may still surround, preferably completely surround, the apertures/windows through which the clinician looks. The advantage of having a support frame is that it is particularly rigid, and can be used to protect the mirror because it extends over its plan area. The fact that the support frame has no glass surfaces, other than the mirror, means that there is no glass to break in it, and no glass to become dirty/obscure. However, another variant is envisaged in which there are actual transparent elements in the window/apertures through which the clinician looks—for example glass.

The support frame for the optical element may circumscribe the optical element, defining one or more window through which the clinician looks in use. The optical element may not be a mirror, but could be a lens with a fibre position behind it. The fibre could enter the attachment for the ophthalmoscope at the 12 o'clock, from above, position. The concept of a frame carrying the optical element and the frame not getting in the way of the image acquired by the image-capturing optics of the ophthalmoscope is advantageous.

Many ophthalmoscopes already have screw threaded holes added in their front—for different purposes. We may size and position the holes in our attachment so as to enable a user to make use of pre-existing holes in the ophthalmoscope to mount the attachment to the ophthalmoscope.

In any, and or all, of the embodiments discussed we may provide the side-on/support member, or the carrier, with an adjustable focusing lens.

No other known design enables the laser beam to be delivered from a point that is actually directly the central beaming access of the binoculars, with no accompanying metal work or other material in the field of vision.

In the embodiment shown in FIG. 5, the laser beam may enter the frame that surrounds the mirror through an aperture in the frame.

Figure 12:
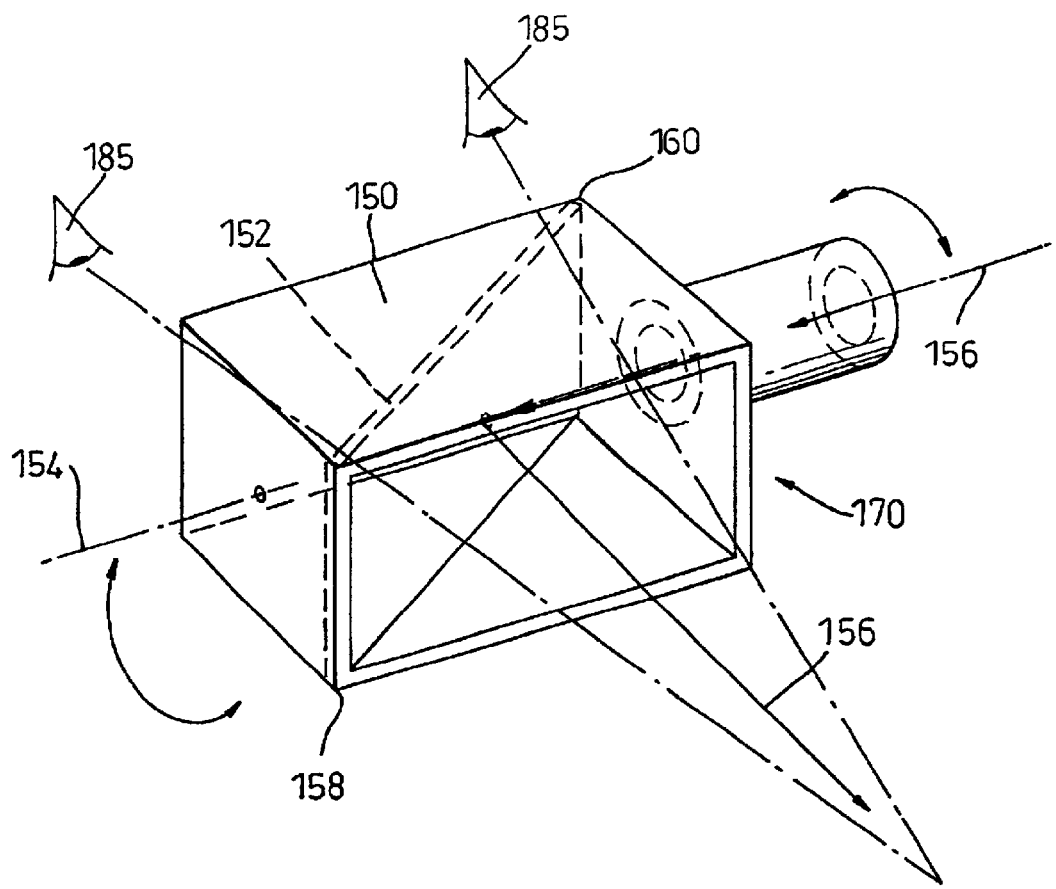
FIGS. 12, 13A to 13C, 14 and 15 show another embodiment of the invention.

FIG. 12 shows another modification. In this example the divergence of the laser beam as it enters the device is too large to allow us to use a small mirror; we want to use a larger mirror to control it/focus it.

FIG. 12 shows a carrier frame 150, or open-ended box, carrying a larger mirror 152, again with the frame 150 being angularly movable about on axis, referenced 154, for controlling the position of the laser beam on the patients eye. The laser beam is referenced 156.

The mirror 152 extends across the whole length of the frame 150, diagonally from corner 158 to corner 160. In another variant it need not extend across the full internal aperture of the carrier.

The mirror 150 reflects the laser beam 156, but is transmissive to at least one/some other optical wavelengths, so that the clinician can look through the mirror 152, through the frame 150. A dichroic mirror with a reflective, non transmissive, characteristic that covers the laser wavelength will achieve the desired result of having the clinician be able to look through the mirror, supported by the frame; and have the mirror reflect the laser beam, and be larger than in FIGS. 10A to 10C. A further benefit is that because the clinician now looks through the optical element that is supported by the frame, and looks past the frame without the frame reducing the field of view, the dichroic mirror can protect the clinicians eyes from unwanted laser reflections. There may be no need to have one or more separate protective dichroic filters for this purpose: the partially reflective (to laser wavelengths), partially transmissive (to other wavelengths) optical element (e.g. mirror, prism, lens, grating or the like), can achieve both desired effects. Alternatively, we may nevertheless provide further protective dichroic filters, e.g. in the eyepieces.

Figure 13A:
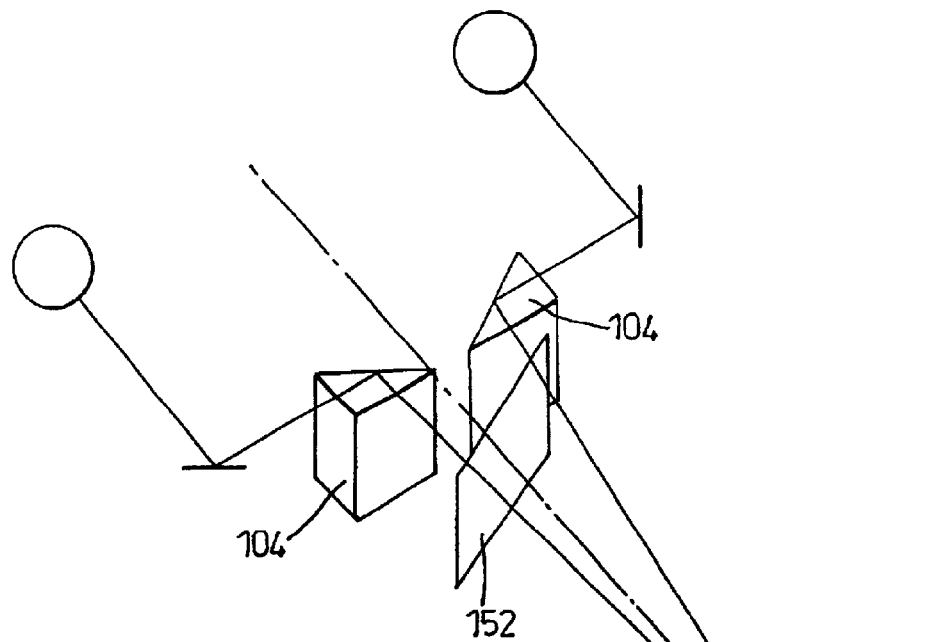
Figure 13B:
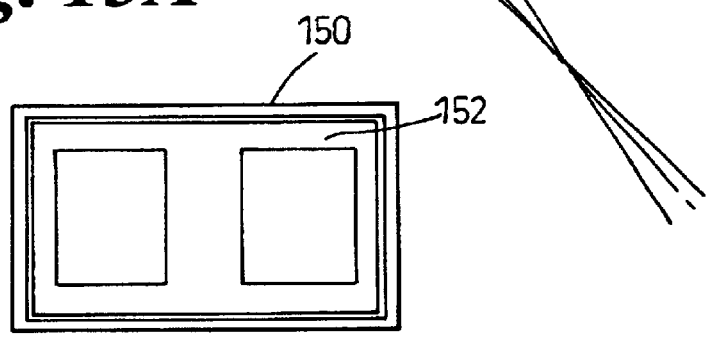
Figure 13C:
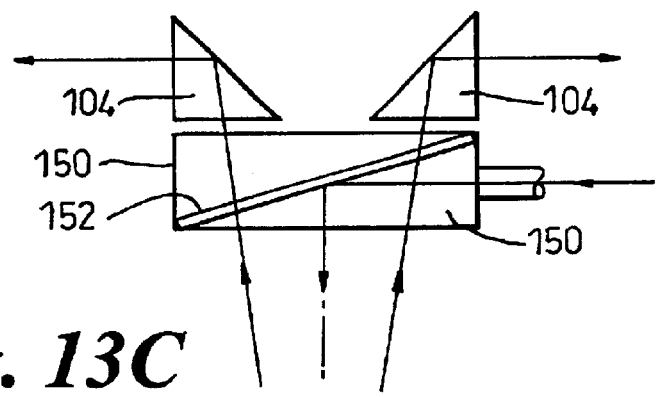

FIGS. 13A to 13C are equivalent to FIGS. 10A to 10C, but for the embodiment of FIG. 12. It will be seen that the carrying frame is outside of the field of view of the clinician, and the clinician looks through the frame and the mirror. In some embodiments the mirror/optical element will be preset and will not be adjustable, but in many embodiments the frame may be moveable to perform movement of the mirror/optical element.

Although the image—capture prisms 104 of FIGS. 13A to 13C are shown spaced apart, they may be abutting. The spacing between the prisms/image capture elements 104 may be adjustable by the clinician. The spacing may be adjustable to keep the image capture element within the carrying frame, and either within the mirror (if it is the dichroic filter/reflection), or operatively laterally at least partially beyond the central mirror (if the central mirror does not transmit).

As will be appreciated, in some embodiments the frame circumscribes a space through which a user looks in use. By having spaced-apart frame regions which hold the mirror at opposed edges the mirror is robustly mounted to the frame. In some embodiments the mirror may be mounted to the frame substantially completely, or completely, around its periphery. In other embodiments the mirror is supported by the frame along substantially the whole of two opposed edges (e.g. upper and lower edges).

Figure 14:
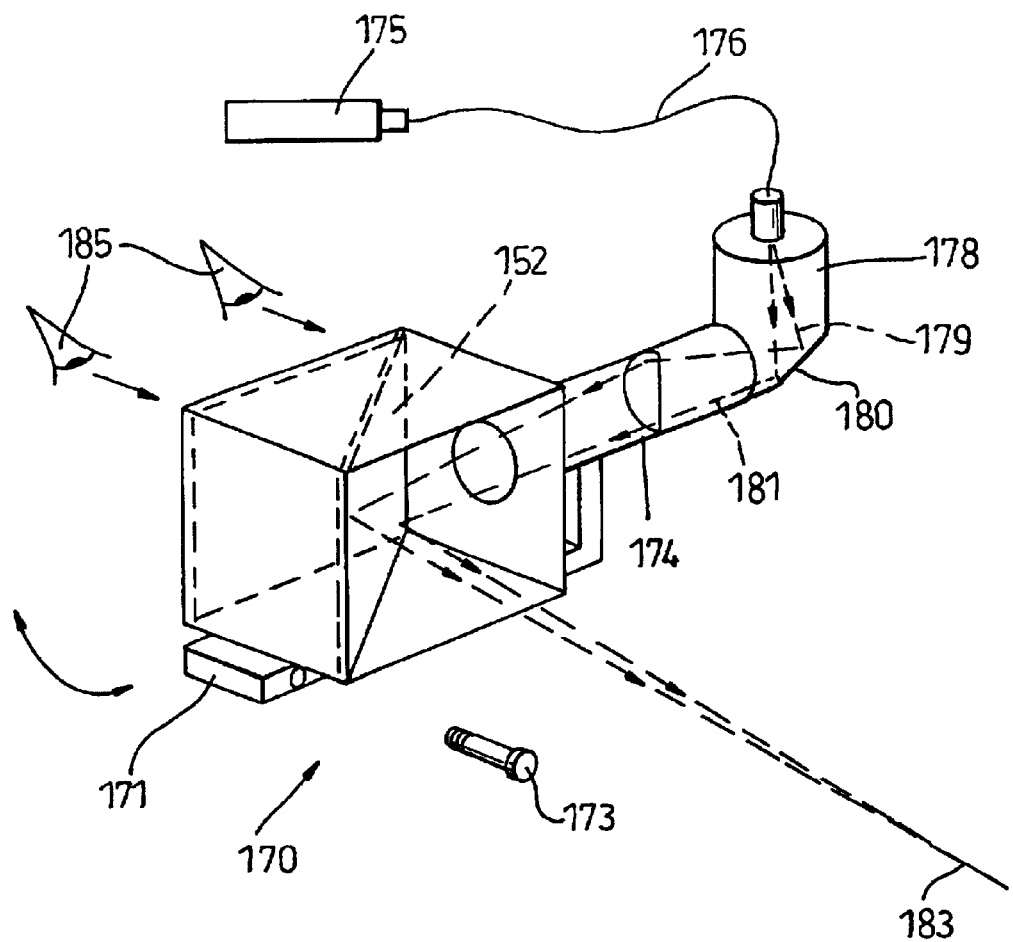

FIG. 14 shows a finer detail of the arrangement of the laser attachment 170 of FIG. 12.

The laser attachment 170 may be readily attached to any conventional indirect ophthalmoscope by way of a bracket 171, and fixed in place by fixing screws 173.

Also depicted is a lens 174 of variable focus, with focus controlled by the user. A laser 175 is coupled to the attachment 170 via fibre 177. A coupling, referenced 178, produces a diverging beam 179 of laser light which is reflected off mirror 180, still diverging at 181. The lens 174 focuses the beam of laser light which is reflected off the mirror 152 to a focal point 183. The focal point is intended to be the retina, or other structure of the patient's eyes, to be burned/treated. The clinician's eyes are referenced 185.

The use of a dichroic mirror can impart a slight colour to the image observed through the mirror, it is therefore preferable that the mirror 152 fills the users entire field of view, such that the image seen is evenly discoloured. If the edge of the mirror 152 can be seen in the users field of view a contrast in colour may be seen which may impede the users vision.

Figure 15:
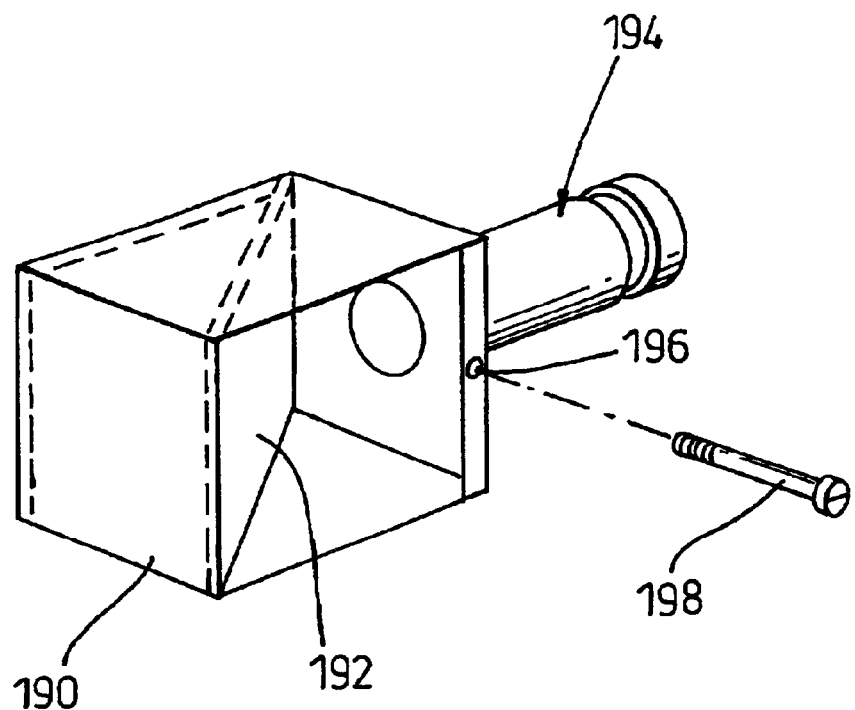

FIG. 15 shows a mirror carrier 190 carrying a mirror 192 angled at 45° sideways, journalled for angular movement by journal 194, and a hole 196 possibly screw threaded, for receiving a turning lever 198 to enable a user to rotate the carrier 190. The lever 198 is normally attached to the carrier 190.

In a preferred embodiment the mirror carrier is configured as a cube in which all sides are approximately 20 mm, and the journal 194 has a diameter of approximately 11 mm.

What is claimed is:

1. A binocular indirect laser ophthalmoscope comprising binocular eyepieces each having an optical axis, said optical axes defining an optical plane, the ophthalmoscope having a central viewing axis lying in said optical plane; and an optical element adapted to position a laser beam into said optical plane substantially on said viewing axis and substantially parallel to said viewing axis.

2. An ophthalmoscope according to claim 1 wherein said optical element is from the group: mirror; prism; lens.

3. An ophthalmoscope according to claim 1 wherein said optical element is provided in a vertical plane and wherein a laser beam emitter is provided laterally to one side of said optical element.

4. An ophthalmoscope according to claim 3 wherein said optical element comprises a mirror and wherein said mirror is inclined at about 45° to a central beam direction of said laterally disposed laser beam emitter.

5. An ophthalmoscope according to claim 1 wherein said optical element is carried by a carrier frame having at least one visual aperture provided therein, said optical axes extending through said visual aperture or apertures.

6. An ophthalmoscope according to claim 5 wherein said frame has two visual apertures provided therein and wherein said optical element is provided between said visual apertures.

7. An ophthalmoscope according to claim 5 wherein said frame defines a visual aperture and wherein each of said optical axes of said eyepieces extends through said aperture.

8. An ophthalmoscope according to claim 4 wherein said mirror is carried by a carrier frame having visual aperture provided therein, said optical axes extending through said visual aperture and said laser mirror being provided extending over said visual aperture.

9. An ophthalmoscope according to claim 5 wherein said carrier frame is bodily movable so as to move the position of said optical element and thereby alter the angle of said laser beam relative to said optical plane.

10. An ophthalmoscope according to claim 8 wherein said carrier frame is bodily movable so as to move the position of said laser mirror and thereby alter the angle of said laser beam relative to said optical plane.

11. An ophthalmoscope according to claim 9 wherein said carrier frame is mounted at one point only thereof for angular movement.

12. An ophthalmoscope according to claim 10 wherein said carrier frame is mounted at one point only thereof for angular movement.

13. An ophthalmoscope according to claim 5 wherein said carrier frame is mounted by a spigot, and said spigot defines a laser-entry aperture through which said laser beam enters said carrier.

14. A binocular laser indirect ophthalmoscope comprising:

a pair of eyepieces for a user to look through, and respective image-capture optics associated with respective eyepieces, said eyepieces and associated image-capture optics having respective optical axes, said optical axes defining an optical plane, and there being a central line of view of said ophthalmoscope lying in said optical plane;

a laser beam coupler for coupling a laser beam delivery device to said ophthalmoscope;

a laser beam director for directing a laser beam provided from said laser beam coupler forwards, away from said ophthalmoscope;

an adjustment mechanism for controlling the position or orientation of said laser beam director so as to vary the position or direction of a laser beam propagating from said director;

and wherein said laser beam coupler is provided disposed laterally to one side of said image capture optics and said laser beam director is provided in front of said image capture optics, and wherein said adjustment mechanism is adjustable to position a laser beam propagating from said director substantially in said optical plane, substantially undivergent therefrom, and substantially on said central line of view.

15. A binocular according to claim 14 wherein said laser beam director is coupled to a mounting coupling allowing relative movement between said director and a support frame or member, said mounting coupling being laterally to one side of said eyepieces.

16. A binocular according to claim 15 wherein said mounting coupling comprises an angularly movable joint.

17. A binocular according to claim 15 wherein said laser beam coupler is provided at said mounting coupling.

18. A binocular according to claim 15 wherein said mounting coupling has a central pivot axis about which said laser beam director is angularly movable, and wherein said laser beam coupler delivers a laser beam substantially on, or parallel to, said pivot axis.

19. A binocular according to claim 18 wherein said laser beam coupler in use aligns an end portion of an optical fibre with said pivot axis.

20. A device for attachment to an indirect ophthalmoscope for fitting a laser to said ophthalmoscope, said device comprising:

a support member;

an attachment formation provided associated with said support member for attaching said support member to said ophthalmoscope;

a laser director coupled to said support member by a mechanical coupling mechanism so as to be movable relative to said support member;

a control mechanism for moving said laser director relative to said support member;

said device has a forward-facing front portion away from which a laser beam is directed in use, and a rearward facing back portion which in use is disposed towards an operator's face, and a side portion laterally disposed to one side of said device;

said mechanical coupling mechanism is provided at said side portion; and wherein said laser beam optical coupler is provided laterally to one side of said device and said laser beam optical coupler and said mechanical coupling mechanism are provided to the same lateral side of said device, and wherein said mechanical coupling mechanism has an axis about which said laser director can be moved angularly, and wherein said laser beam coupler is provided at said axis.

21. A device for attachment to an indirect ophthalmoscope for fitting a laser to said ophthalmoscope, said device comprising:

a support member;

an attachment formation provided associated with said support member for attaching said support member to said ophthalmoscope;

a laser director coupled to said support member by a mechanical coupling mechanism so as to be movable relative to said support member;

a control mechanism for moving said laser director relative to said support member; wherein said device has a forward-facing front portion away from which a laser beam is directed in use, and a rearward facing back portion which in use is disposed towards an operator's face, and a side portion laterally disposed to one side of said device, said mechanical coupling being provided at said side portion;

said laser director comprises a carrier and an optical element supported on said carrier; and said mechanical coupling mechanism has an axis about which said laser director can be moved angularly, and wherein said laser beam coupler is provided at said axis.

22. A device for attachment to an indirect ophthalmoscope for fitting a laser to said ophthalmoscope, said device comprising:

a support member;

an attachment formation provided associated with said support member for attaching said support member to said ophthalmoscope;

a laser director coupled to said support member by a mechanical coupling mechanism so as to be movable relative to said support member;

a control mechanism for moving said laser director relative to said support member; wherein said device has a forward-facing front portion away from which a laser beam is directed in use, and a rearward facing back portion which in use is disposed towards an operator's face, and a side portion laterally disposed to one side of said device, said mechanical coupling mechanism being provided at said side portion;

said laser director comprises a carrier and an optical element supported on said carrier; and said mechanical coupling mechanism has an axis about which said laser director can be moved angularly, and wherein said laser beam coupler is provided at said axis; and wherein said laser director has a first window portion registerable with a first image-capturing optical aperture of said binocular ophthalmoscope and a second window portion registerable with a second image-capturing optical aperture of said ophthalmoscope, and wherein said optical element is provided either (i) between said first and second windows; or (ii) overlying said first and second window portions.

23. A method of aligning a laser beam of an indirect binocular laser ophthalmoscope with a visual plane of said ophthalmoscope defined by first and second optical axes of first and second eyepiece optics of said binocular ophthalmoscope, said method comprising providing a reflector between said optical axes such that said reflector intersects said visual plane;

directing a laser beam onto said reflector at about the position where said reflector intersects said visual plane;

and controlling the orientation or position of said reflector so as to cause a laser beam reflected from said reflector to be in or parallel to said visual plane.

24. A method of aligning a laser beam of an indirect binocular laser ophthalmoscope with a visual plane of said ophthalmoscope defined by first and second optical axes of first and second eyepiece optics of said binocular ophthalmoscope, said method comprising providing a beam manipulator between said optical axes, such that said beam manipulator intersects said visual plane, and causing said laser beam to enter said ophthalmoscope laterally to one side thereof.

25. A binocular indirect ophthalmoscope having first and second image capture optics having respective first and second optical pathways which define a viewing plane, and delivery means for delivering a laser beam to an optical element located adjacent said image capture optics for causing said laser beam to be emitted in a direction substantially in said viewing plane, undivergent therefrom, wherein said optical element comprises a mirror mounted as a central bridge piece in a cage which defines viewing openings in register with a said image capture optics and to each side of said mirror surface.

26. A binocular indirect ophthalmascope having first and second image capture optics having respective first and second optical pathways which define a viewing plane, and delivery means for delivering a laser beam to an optical element located adjacent said image capture optics for causing said laser beam to be emitted in a direction substantially in said viewing plane, undivergent therefrom, wherein a carrying frame is provided and wherein said optical element comprises a dichroic mirror peripherally supported by said carrying frame and extending over a substantial part of a visual aperture provided in said carrying frame, a user looking through said dichroic mirror and through said visual aperture in use, and wherein said frame is adjustable in angle about an axis in or parallel to said viewing plane and substantially normal to a central viewing axis of said ophthalmoscope.

27. A binocular indirect ophthalmoscope having first and second image capture optics having respective first and second optical pathways which define a viewing plane, and delivery means for delivering a laser beam to an optical element located adjacent said image capture optics for causing said laser beam to be emitted in a direction substantially in said viewing plane, undivergent therefrom, wherein:

a carrying frame is provided and wherein said optical element comprises a dichroic mirror peripherally supported by said carrying frame and extending over a substantial part of a visual aperture provided in said carrying frame, a user looking through said dichroic mirror and through said visual aperture in use;

said frame is adjustable in angle about an axis in or parallel to said viewing plane and substantially normal to a central viewing axis of said ophthalmoscope; and said laser beam is delivered substantially normally to said viewing plane and is reflected into that plane by a mirror mounted to said cage.

28. A binocular indirect ophthalmoscope having first and second image capture optics having respective first and second optical pathways which define a viewing plane, and delivery means for delivering a laser beam to an optical element located adjacent said image capture optics for causing said laser beam to be emitted in a direction substantially in said viewing plane, undivergent therefrom, wherein:

said optical element comprises a mirror mounted as a central bridge piece in a case which defines viewing openings in register with a said image capture optics and to each side of said mirror surface;

and further including dichroic filters provided at eyepieces of said binocular.

29. A binocular indirect ophthalmoscope whose eyepieces have optical axes which define a viewing plane, a mirror carrier frame which has a viewing opening or window registered with said eyepieces and has a dichroic mirror mounted in that viewing plane extending across said viewing opening, and delivery means for delivering a laser beam to said mirror for reflection into said viewing plane and along a central viewing axis of said ophthalmoscope.

30. An accessory for a binocular indirect ophthalmoscope which comprises a frame having a viewing aperture and an optical element disposed across said viewing aperture, said optical element being adapted to reflect light of a selected laser wavelength and transmit light of at least another selected optical wavelength such that in use a user is able to look through said viewing aperture and through said optical element wherein said frame is mounted on a fixing bracket so that it can pivot about an axis leading across said viewing aperture.

* * * * *